United States Patent [19]

Selin

[11] 4,401,826

[45] Aug. 30, 1983

[54] METHOD FOR PRODUCTION OF MERCAPTO FUNCTIONAL SILANES

[75] Inventor: Terry G. Selin, Schenectady, N.Y.

[73] Assignee: General Electric Company, Waterford, N.Y.

[21] Appl. No.: 416,577

[22] Filed: Sep. 10, 1982

[51] Int. Cl.$^3$ ............................ C07F 7/08; C07F 7/18
[52] U.S. Cl. .................................................. 556/429
[58] Field of Search ....................................... 556/429

[56] References Cited

U.S. PATENT DOCUMENTS

| Re. 28,129 | 8/1974 | Rakus et al. | 556/429 |
| 3,314,982 | 4/1967 | Koerner et al. | 556/429 |
| 3,382,196 | 5/1968 | Gowdy et al. | 260/3 |

FOREIGN PATENT DOCUMENTS 1102251  2/1965  United Kingdom .

OTHER PUBLICATIONS

Industrial Phamplet, "Silane Coupling Agents," Dow Corning Corp.

Primary Examiner—Paul F. Shaver
Attorney, Agent, or Firm—Hedman, Casella, Gibson, Costigan & Hoare

[57] ABSTRACT

An improved method for the production of mercapto functional silanes is provided whereby reactions between haloalkyl silanes and thioureido compounds in the presence of ammonia are accelerated with tertiary nitrogen-containing compounds. In a preferred embodiment the reaction of 3-chloropropyltrimethoxysilane with thiourea is accelerated by N,N-dimethylformamide and other compounds to produce 3-mercaptopropyltrimethoxysilane at lower temperatures and with increased yield.

11 Claims, No Drawings

METHOD FOR PRODUCTION OF MERCAPTO FUNCTIONAL SILANES

BACKGROUND OF THE INVENTION

This invention relates to the production of mercapto functional silanes. More specifically, it relates to the use of tertiary nitrogen-containing compounds to accelerate known reactions between haloalkyl silanes and thioureido compounds in the presence of ammonia or other alkaline compounds (such as sodium methoxide, amines, etc.) to yield mercapto functional silanes.

Silane coupling agents have become important compounds in industrial applications involving reinforcement of composites, such as filled plastics, and strong bonding between organic and inorganic materials. Mercapto functional silanes have been found especially useful as coupling agents in treating fillers for EPDM elastomers and in treating metal surfaces. "Silane Coupling Agents," a Dow Corning technical publication (copyright 1970, Dow Corning Corporation) and British Pat. No. 1,102,251 (Union Carbide), both incorporated herein by reference, describe such uses.

Mercapto functional silanes are typically produced by substitution of sulfur for halogen atoms in haloalkyl silanes, a favored method being reaction of a haloalkyl silane with a thioureido compound, such as thiourea, in the presence of ammonia. Although this method has the advantages of requiring no solvents and simple recovery of the product, there are disadvantages in that the reaction rate is slow and the recovery is only around 80%.

It has now been discovered that these disadvantages can be overcome by employing as an accelerator in the abovedescribed reactions certain tertiary nitrogen-containing compounds, including carbamides and diamines. These compounds have been found to accelerate the substitution reaction, allowing lower reaction temperatures, significantly descreasing the reaction time and increasing the yield of pure mercapto functional silanes to around 90% or more.

SUMMARY OF THE INVENTION

Accordingly, it is an object of the present invention to provide an improved method for producing mercapto silanes.

It is a further object of the present invention to provide new methods for producing mercapto functional silanes.

These and other objects are accomplished in a method for producing mercapto functional silanes comprising reacting a haloalkyl silane with a thioureido compound in the presence of ammonia or other alkaline materials by the improvement comprising carrying out said reaction in the presence of a tertiary nitrogen-containing compound.

DETAILED DESCRIPTION OF THE INVENTION

Silanes useful as coupling agents, including the mercaptosilanes produced by the improved method of this invention, are organosilicon monomers which typically possess dual functionality. Hydrolyzable and hydrolytically stable groups appear in the same molecule. The general formula for such monomers is $R-SiX_3$, where R is a thermally and hydrolytically stable organofunctional group, and X is a hydrolyzable group. Most commonly, the R group is separated from the silicon atom by an alkyl residue, such as a propylene ($-CH_2CH_2CH_2-$) chain, and X is an alkoxy group, such as methoxy ($-OCH_3$). Typical R groups which can be found in the art include amino, organoamino, polyamino, methacrylate, vinyl, and haloalkyl groups. The silanes produced according to the present invention are mercapto functional; the most common, and preferred, product is 3-mercaptopropyltrimethoxysilane, $HS(CH_2)_3Si(OCH_3)_3$.

One advantageous means of producing mercapto functional silanes such as 3-mercaptopropyltrimethoxysilane (3-MPTS) is by reacting the analagous halo functional silane, e.g., 3-chloropropyltrimethoxysilane (3-CPTS), with a sulfur source, usually a thioureido compound (containing the radical $H_2N.CS.NH-$), in the presence of alkali, such as ammonia ($NH_3$). This type of reaction could be illustrated as follows:

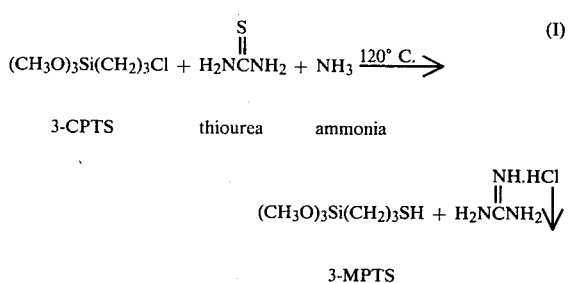

The reaction (I) is favored because it does not require solvents and the crude product is simply decanted from the solid hydrochloride salt. Purification of the product is completed by fractional distillation at reduced pressure.

Disadvantages of the reaction (I) are that the yield is only around 80% and it is impractically slow: At temperatures below 100° C., no reaction is observed; and even at the optimal reaction temperature of 120° C., 10-14 hours are required for completion. At temperatures above 140° C., side reactions occur which cut the yield considerably.

Substitution of a structurally similar source of sulfur, thiosemicarbazide ($H_2N.CS.NHNH_2$), has been attempted, as follows:

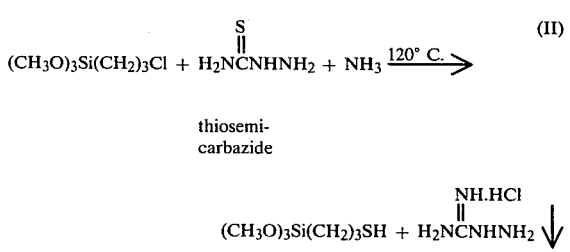

However, at 120° C. no reaction occurs; and at higher temperatures 135°–150° C., only minor amounts of 3-mercaptopropyltrimethoxysilane are produced.

Certain tertiary nitrogen-containing compounds will accelerate this type of reaction such that mercaptosilane can be produced with increased yield at lower temperatures. To illustrate, reactions I and II, above, could be represented as follows:

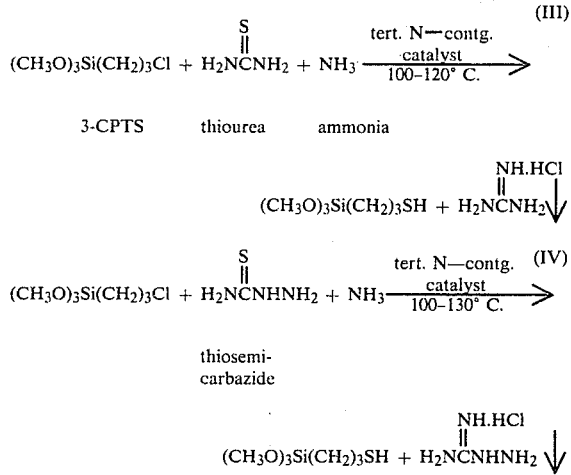

The mercaptosilane product is recovered in the same way, by simple decanting of the silane from the solid hydrochloride salt, followed by purification by fractional distillation at reduced pressure. The yield from the catalyzed reactions is typically in the range of about 80 to 90%.

The tertiary nitrogen-containing compounds suitable for the purposes herein are linear and ring structures containing a radical —RNR$_2$, wherein R can be the same or different hydrocarbon, carboxy, or carbamoyl radical, the compounds including (but not limited to) carbamides, carbazides, and diamines. Specific examples of these compounds include N,N-dimethylformamide, N,N-dimethylacetamide, N-methylpyrrolidone, N,N,N',N'-tetramethylurea, N,N,N',N'-tetramethylethylenediamine. N,N-dimethylformamide and N-methylpyrrolidone are preferred.

The proportion of tertiary nitrogen-containing accelerator employed is not critical to the present invention. In general, as with any additive, practicioners will prefer to use the smallest amount which will bring about the desired effect. However, by way of illustration, 5 to 22 parts per 100 parts of total reaction mixture have been found suitable to accomplish the purposes of the invention herein. Likewise, the point at which the accelerator is added is not critical, although inclusion of the additive in the original charging of the reaction vessel with the other ingredients may be most convenient, and for this reason is preferred.

In order that persons skilled in the art may more easily practice the present invention, the following examples, demonstrating reactions III and IV discussed above, are provided by way of illustration and not by way of limitation.

EXAMPLE 1

A reaction vessel was charged with 198 parts by weight of 95% pure 3-chloropropyltrimethoxysilane, 90 parts by weight thiourea, and 20 parts by weight N,N-dimethylformamide. A slow stream (about 2 ml./sec.) of anhydrous ammonia was introduced below the surface of the reaction mixture via an inlet tube. While the ammonia flow was maintained, the mixture was stirred and heated at 110° C. for a period of 9 hours, after which gas chromotography analysis indicated that 97% of the 3-chloropropyltrimethoxysilane had reacted.

The mixture was allowed to cool. Excess thiourea and hydrochloride by-products formed a second liquid phase. When stirring was stopped the liquid salt phase (bottom layer) crystallized to a solid mass at room temperature. The crude 3-mercaptopropyltrimethoxysilane (178 parts by weight product) was decanted from the solid as a nearly clear, colorless liquid into a distillation flask. Fractional distillation at reduced pressure using a 30-centimeter glass helices-packed column provided 156 part by weight of 3-mercaptopropyltrimethoxysilane boiling at 122°–126° C. at 40 mm Hg. Analysis of the distilled product indicated a purity of about 97%.

The same reaction was conducted in the absence of the N,N-dimethylformamide accelerator. Under the above conditions, only 18% of the 3-chloropropyltrimethoxysilane was converted to the mercaptan.

N,N-dimethylacetamide, N-methylpyrrolidone, N,N,N',N'-tetramethylurea, N,N,N',N'-tetramethylethylenediamine was evaluated in the same manner as Example I and found to be useful accelerators for the reaction.

EXAMPLE 2

A reaction vessel was charged with 198 parts by weight of 3-chloropropyltrimethoxysilane, 109 parts by weight thiosemicarbazide, and 25 parts by weight N,N-diemthylformamide. A slow stream (about 2 ml./sec.) of anhydrous ammonia was introduced below the surface of the reaction mixture via an inlet tube. While the ammonia flow was maintained, the mixture was stirred and heated at 120° C. for a period of 9 hours. The temperature during the first 4 hours had to be controlled carefully because the reaction tended to be mildly exothermic. After the 9 hour heating period, GC analysis indicated that 95% of the 3-chloropropyltrimethoxysilane had reacted.

The mixture was allowed to cool. The crude 3-mercaptopropyltrimethoxysilane (188 parts by weight product) was decanted from the solids as a nearly clear, colorless liquid into a distillation flask. Fractional distillation at reduced pressure utilizing a 30 centimeter glass helices-packed column provided 170 parts by weight 3-mercaptopropyltrimethoxysilane boiling at 122°–126° C. at 40 mm Hg. Analysis of the distilled product indicated a purity of about 97%.

I claim:

1. In a method for producing mercapto functional silane comprising reacting a haloalkyl silane and a thioureido compound in the presence of ammonia, the improvement comprising carrying out said reaction in the presence of a tertiary nitrogen-containing compound.

2. The method of claim 1, wherein said mercapto functional silane is 3-mercaptopropyltrimethoxysilane.

3. The method of claim 2, wherein said thioureido compound is selected from the group consisting of thiourea and thiosemicarbazide.

4. The method of claim 3, wherein said tertiary nitrogen-containing compound is selected from the group consisting of N,N-dimethylformamide, N,N-dimethylacetamide, N-methylpyrrolidone, N,N,N',N'-tetramethylurea, and N,N,N',N'-tetramethylethylenediamine.

5. The method of claim 4, wherein said tertiary nitrogen-containing compound is N,N-dimethylformamide.

6. The method of claim 4, wherein said tertiary nitrogen-containing compound is present in the reaction in an amount of from about 5 to 22 parts per 100 parts of the total reaction mixture.

7. An improved method for the production of mercapto functional silanes comprising:
  (i) mixing in a reaction vessel:
    (a) 60 to 70 parts by weight of a haloalkyl silane,
    (b) 25 to 35 parts by weight of a thioureido compound,
    (c) 6.5 to 22 parts by weight of a tertiary nitrogen-containing compound;
  (ii) introducing continuously into the reaction mixture anhydrous ammonia;
  (iii) heating said mixture until sufficient haloalkyl silane is converted to mercapto functional silane;
  (iv) removing said mercapto functional silane from said reaction vessel; and
  (v) purifying the mercapto functional silane by distillation.

8. The method of claim 7, wherein the haloalkyl silane (a) is 3-chloropropyltrimethoxysilane; the thioureido compound (b) is selected from the group consisting of thiourea and thiosemicarbazide; the tertiary nitrogen-containing compound (c) is selected from the group consisting of N,N-dimethylformamide, N,N-dimethylacetamide, N-methylpyrrolidone, N,N,N',N'-tetramethylurea, and N,N,N',N'-tetramethylethylenediamine; and the mercapto functional silane product is 3-mercaptopropyltrimethoxysilane.

9. The method of claim 8, wherein said thioureido compound is thiourea.

10. The method of claim 8, wherein said thioureido compound is thiosemicarbazide.

11. The method of claim 9 or 10, wherein said tertiary nitrogen-containing compound is N,N-dimethylformamide.

* * * * *